(12) United States Patent
Gouma et al.

(10) Patent No.: US 7,981,215 B2
(45) Date of Patent: Jul. 19, 2011

(54) ELECTROSPUN SINGLE CRYSTAL MOO₃ NANOWIRES FOR BIO-CHEM SENSING PROBES

(75) Inventors: Pelagia-Irene Gouma, Port Jefferson, NY (US); Aisha Suzette Haynes, Far Rockaway, NY (US); Krithika Kalyanasundaram, Stony Brook, NY (US)

(73) Assignee: The Research Foundation of State University of New York, Albany, NY (US)

( * ) Notice: Subject to any disclaimer, the term of this patent is extended or adjusted under 35 U.S.C. 154(b) by 75 days.

(21) Appl. No.: 12/301,580

(22) PCT Filed: May 22, 2007

(86) PCT No.: PCT/US2007/012342
§ 371 (c)(1),
(2), (4) Date: Nov. 19, 2008

(87) PCT Pub. No.: WO2007/139859
PCT Pub. Date: Dec. 6, 2007

(65) Prior Publication Data
US 2009/0110926 A1    Apr. 30, 2009

Related U.S. Application Data

(60) Provisional application No. 60/802,472, filed on May 22, 2006.

(51) Int. Cl.
*C30B 7/00* (2006.01)
(52) U.S. Cl. .............. 117/75; 117/11; 117/12; 117/73

(58) Field of Classification Search .............. 117/11, 117/12, 73, 75
See application file for complete search history.

(56) References Cited

FOREIGN PATENT DOCUMENTS
WO    WO 2007/073111 A    6/2007

OTHER PUBLICATIONS

Sawicka et al."Molybdenum and Tungsten Oxide Nanowires Prepared by Electrospinning", Mater. Res. Soc. Symp. Proc. vol. 847 © 2005 Materials Research Society.*
Li et al: Nanofibers and Nanoplatelets of MoO3 Via an Electrospinning Technique Journal of Physics and Chemistry of Solids, Pergamon Press, London, GB, vol. 67, No. 8, Aug. 2006, pp. 1869-1872, XP005575843 ISSN: 0022-3697 p. 1869, col. 2, Line 21-p. 1870, col. 1, Line 27.
Gouma P et al: Electrospun Single-Crystal MoO3 Nanowires for Biochemistry Sensing Probes Journal of Materials Research Mater. Res. Soc USA, vol. 21, No. 11, Nov. 2006, pp. 2904-2910, XP002459617 ISSN: 0884-2914 p. 2905, col. 1, Line 36-p. 2906, col. 1, Line 7; Figure 1,2.

(Continued)

Primary Examiner — Matthew J Song
(74) Attorney, Agent, or Firm — Medlen & Carroll, LLP

(57) ABSTRACT

Single crystal $M_oO_3$ nanowires were produced using an electrospinning technique. High resolution transmission electron microscopy (HRTEM) revealed that the 1-D nanostructures are from 10-20 nm in diameter, on the order of 1-2 μm in length, and have the orthorhombic $M_oO_3$ structure. The structure, crystallinity, and sensoric character of these electrostatically processed nanowires are discussed. It has been demonstrated that the non-woven-network of $M_oO_3$ nanowires exhibits higher sensitivity and an n-type response to $NH_3$ as compared to the response of a sol-gel based sensor.

4 Claims, 5 Drawing Sheets

OTHER PUBLICATIONS

Sawicka K M et al: Molybdenum and Tungsten Oxide Nanowires Prepared by Electrospinning Organic/Inorganic Hybrid Materials-2004. (Materials Research Society Symposium Proceedings vol. 847) Materials Research Society Warrendale, PA, USA, 2005, pp. 557-562, XP002459649 ISBN: 1-55899-795-4 p. EE9.46.2, Line 3—p. EE9.46.5, Line 13.
Int'l Search Report (PCT/ISA/210) in PCT/US2007/012342 (4pp).
PCT Written Opinion (PCT/ISA/237) in PCT/US2007/012342 (7pp).
Dharmaraj, N., et al. Materials Chemistry and Physics 87, (2004) 5-9. *Nickel titanate nanofibers by electrospinning*.
Dharmaraj, N., et al. Inorganic Chemistry Communications 7 (2004) 431-433. *Preparation and morphology of magnesium titanate nanofibres via electorspinning*.
Gouma, P.I., et al. J. Am. Ceram. Soc. 84 [3] 619-22 (2001) *Anatase-to-Rutile Transformation in Titania Powers*.
Gouma, P.I., et al. NanoStructured Materials, vol. 11, No. 8, pp. 1231-1237, 1999. *Structural Stability of Titania Thin Films*.
Guan, Hongyu, et al. Materials Chemistry and Physics 82 (2003) 1002-1006. *A novel method for preparing CO3O4 nanofibers by using electrospun PVA/cobalt acetate composite fibers as precursor*.
Li, Dan, et al. Nano Letters 2003 vol. 3, No. 4 555-560. *Fabrication of Titania Nanofibers by Electrospinning*.
Prasad, A.K., et al. Sensors and Actuators B 93 (2003) 25-30. *Comparison of sol-gel and ion beam deposited MoO3 thin film gas sensors for selective ammonia detection*.
Prasad, A.K., et al. Thin Solid Films 436 (2003) 46-51. *Reactively sputtered MoO3 films for ammonia sensing*.
Tomer, V., et al. Solar Energy Materials & Solar Cells 85 (2005) 477-488. *Selective emitters for thermophotovoltaics: erbia-modified electrospun titania nanofibers*.
Viswanathamurthi, P., et al. Scripta Materialia 49 (2003) 577-581. *Vanadium pentoxide nanofibers by electrospinning*.
Viswanathamurthi, P., et al. Inorganic Chemistry Communications 7 (2004) 679-682. *Ruthenium doped TiO2 fibers by electrospinning*.
Viswanathamurthi, P., et al. Materials Letters 58 (2004) 3368-3372. *Preparation and morphology of palladium oxide fibers via electrospinning*.
Sawicka, K. M., et al. Sensor Letters, vol. 3, 1-5, 2005. *Metal Oxide Nanowires for Use in Chemical Sensing Applications*.

\* cited by examiner

ELECTROSPUN SINGLE CRYSTAL MOO₃ NANOWIRES FOR BIO-CHEM SENSING PROBES

PRIORITY

This application claims priority to application Ser. No. 60/802,472, which was filed with the U.S. Patent and Trademark Office on May 22, 2006.

BACKGROUND

1. Field of the Invention

The present invention generally relates to an electrospinning method for making single crystal $MoO_3$ nanowires, nanowires made from said process and to bio-chem sensing probes comprising the nanowires of the invention.

2. Background of the Invention

One-dimensional metal oxides are the focus of current research efforts in nanotechnology as they promise improved electro-optical, electro-chromic, catalytic, and gas sensing properties. The large surface area to volume ratio of nanofibers and nanowires suggest improvement of adsorption and reaction rates of gas sensitive materials. Electrospinning is a novel nanomanufacturing technique used to process metal oxide nanofiber networks. Titanium dioxide was among the first metal oxides that were processed by means of electrospinning into composite nanofibers. Li and Xia, NanoLetters, (2003), 3(4), 555-560. In the method of Li and Xia, titania sol-gel was directly added to an alcohol solution containing polyvinylpyrrolidone (PVP) and was electrospun to form non-woven mats. Polycrystalline metal oxide nanofibers were achieved by a heat treatment at 500° C. in air for three hours.

Madhugiri and Sun et al. combined the methodology for forming mesoporous $TiO_2$ with electrospinning to produce mesoporous titanium dioxide fibers Electrospun mesoporous titanium dioxide fibers. S. Madhugiri, B. Sun, P. G. Smirniotis and J. P. Ferraris: Microporous and Mesoporous Materials, (2004), 69, p. 77.

Most recently long titania nanofibers and those modified with erbium oxide were fabricated by electrospinning followed by thermal pyrolysis. V. Tomer, R. Teye-Mensah, J. C. Tokash and N. Stojilovic: Solar Energy Materials and Solar Cells, (2005), 85(4), 477-488.

Other groups have also reported the synthesis of numerous other metal oxide nanofibers prepared by electrospinning. They have successfully electrospun polyvinyl acetate (PVAc) with vanadium sol-gel to create composite nanofibers, and calcinations of the as received membranes resulted in pure vanadium pentoxide nanofibers. Viswanathamurthi and Bhattaij et al., Scripta Materialia, (2003), 49, 577-581. A similar procedure was followed for magnesium titanate, Dharamaraj and Park et al. Inorg Chem Comm. (2004), 7, 431; p-type semiconducting palladium oxide, Viswanathamurthi and Bhattarai et al., Materials Letters, (2004), 58, 3368-3372; nickel titanate, Dharmaraj and Park et al. Materials Chemistry and Physics, (2004). 87: 5-9, and ruthenium doped titanium dioxide, Viswanathamurthi and Bhattaij et al., Inorg Chem Comm, (2004), 7, p. 679.

Shao et al. have electrospun polyvinyl alcohol (PVA) mixed with various metal oxide solutions to create metal oxide composite nanofibers, followed by calcinations of precursor membranes to result in pure metal oxide nanowires. To date, their group has successfully synthesized $Co_3O_4$, NiO, CuO, $Mn_2O_3$, $Mn_3O_4$, ZnO, $ZrO_2$, NiO/ZnO, $NiCo_2O_4$, $CeO_2$, and $LiMn_2O_4$ nanofibers e.g., Materials Chemistry and Physics, (2003), 82, p. 1002-1006. The common characteristic for all published work on electrospun metal oxide nanofiber formation is the polycrystalline grain morphology seen along the decomposed polymer frame of the heat-treated composite fibers. The present document, however, has focuses on the breakthrough synthesis of single crystal metal oxide nanowires for gas sensing applications.

There are several reasons why single crystal nanowires perform better than their polycrystalline counterparts, as far as their gas sensing properties are concerned. The first reason is gas selectivity. Semiconducting oxides exhibit strong affinity to specific compounds as a function of their polymorphic structure or crystallographic arrangement. Since polycrystalline materials are homogeneous with respect to the type of crystal planes and directions exposed to the gas, there is limited gas selectivity and a lot of cross-interference from other gases observed. In contrast, single crystals are usually grown along preferred crystal planes and directions, so gas sensors based on them may markedly improve their gas sensing selectivity. The second reason is stability. Single crystalline nanowires are usually stoichiometrically better defined and have a greater level of crystallinity than the multigranular oxides currently used in sensors, they may potentially reduce the instability associated with defects forming at grain boundaries.

Finally, single crystalline nanowires have many advantages in many other applications. For example, light emitting devices and field emission devices based on single crystalline semiconducting oxide nanowires have much stronger signal intensities than polycrystals.

SUMMARY OF THE INVENTION

The present invention is generally directed to a method for producing electrospun single crystal $MoO_2$ nanowires, to the nanowires produced from said process, and to devices comprising said nanowires, e.g., bio-chem sensing probes. The invention is also directed to the $MoO_3$ highly sensitive and selective probes produced from the method.

DETAILED DESCRIPTION OF THE FIGURES

The above and other objects, features and advantages of certain exemplary embodiments of the present invention will be more apparent from the following detailed description taken in conjunction with the accompanying drawings, in which.

DETAILED DESCRIPTION OF THE INVENTION

Figure 1:
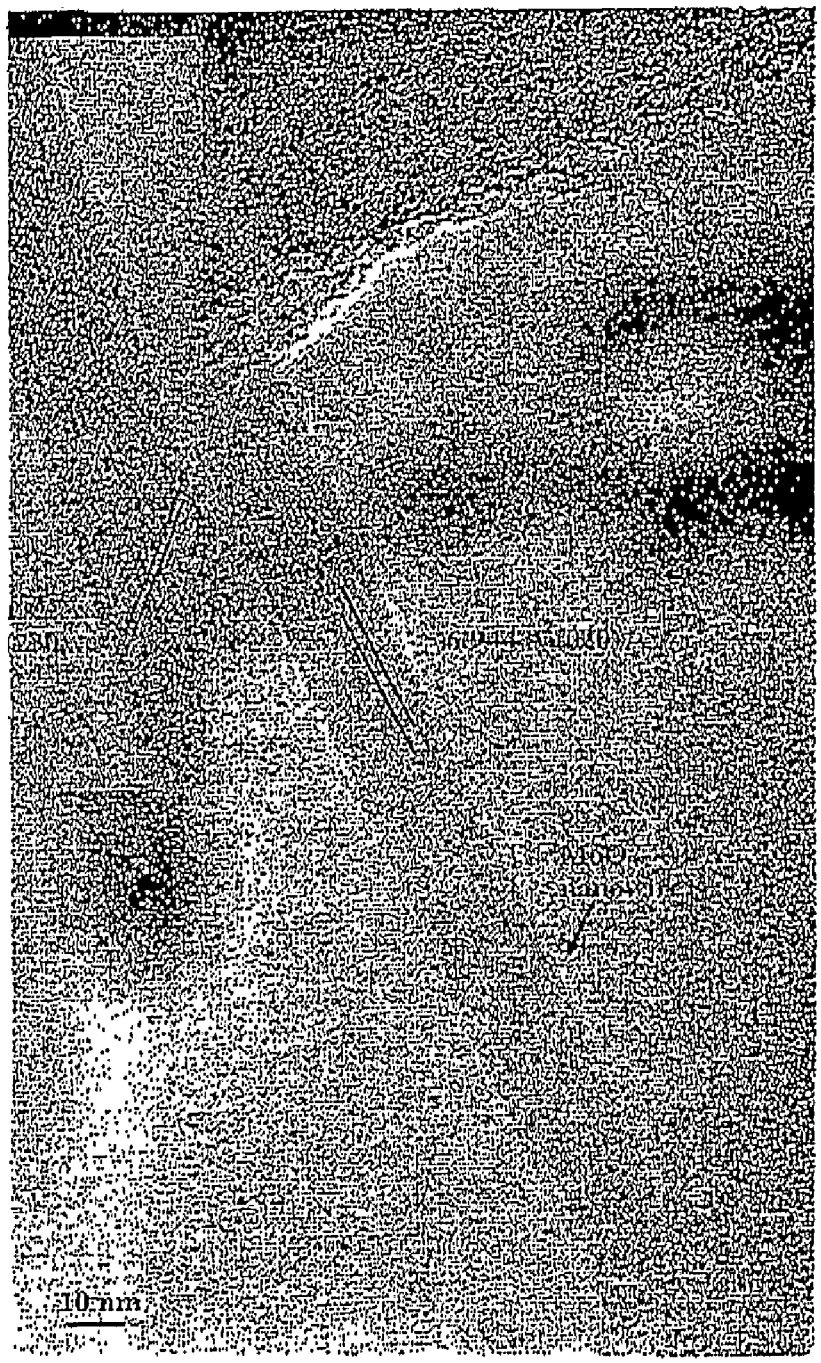
FIG. 1 illustrates the morphology and structure of the $MoO_3$ nanowire deposited on $Si_3N_4$ grid with the inset magnified at a higher magnification.

A description of detailed construction of preferred embodiments of electrospun single crystal $MoO_3$ nanowires and their gas sensing properties is provided to assist in a comprehensive understanding of exemplary embodiments of the invention. These electrospun single crystal $MoO_3$ nanowires are discussed and compared with those of the sol-gel precursor material. Those of ordinary skill in the art will recognize that various changes and modifications of the embodiments described herein can be made without departing from the scope and spirit of the invention. Descriptions of well-known functions and constructions are omitted for clarity and conciseness.

The $MoO_3$ nanowires of the invention can be produced using the following representative procedure according to the invention.

Molybdenum isopropoxide nanoparticles are first suspended in a solution of 10 ml of butanol for preparation of 0.5 Molar concentration. 1.3 grams of polyvinylpyrrolidone (PVP) is dissolved in 10 ml of ethanol to make 0.1 mM concentration of PVP. The molybdenum isopropoxide ($MoO_3$) solution is then centrifuged for 5 minutes and 2 ml of the solvated mixture (without dissolved particulates) is mixed with 8 ml of the 0.1 mM PVP solution. The solution is then electrospun onto aluminum foil in air using a DC voltage power supply (Gamma High Voltage Research, Model ES 30P-6W), a programmable syringe pump (KD Scientific, Model 200), and an aluminum collector plate. The solution is electrospun under conditions effective to form films. The present inventors have found that electrospinning at a voltage of about 20 KV, with a needle to collector distance of 100 mm, and with a 22 gauge needle to be particularly effective. The films are then placed on alumina substrates and calcined. Typical calcining conditions are from 25° C. to 500° C. for about two hours, followed by stabilization for approximately 8 hours at 500° C. and then a cooling down period from 500° C. to 25° C. in about 2 hours. The calcined mat is then dissolved in ethanol and the solution is ultrasonicated for several minutes to break up the particles and properly dissolve any remaining polymer. The solution is then deposited onto an alumina substrate with gold interdigitated electrodes with 20 um spacings forming a thin film of single crystalline nanowires.

The 1-D nanowire thin film have shown to have a 10% increase insensitivity over the comparable $MoO_3$ sol-gel thin film sensor. The unique features of this technology include [a] sensitive oxide nanoprobes with dimensions ranging from 10-15 nm in diameter and several microns in length [b] quasi 1-D nanoarchitectures with increased sensitivity over the traditional sol-gel sensor technology and [c] oxide nonowires with specific crystalline phases and oxidations states manipulated by changing the calcinations process resulting in high analyte specificity.

This electrospinning technique offers the advantage of a single step top down approach to making single crystallince $MoO_3$ nanowires with high specificity to select biological or chemical agents through manipulation of crystal structure. Each nanowire can be used as an individual sensing probe for bio-chem sensing applications. An array of 1000's of these nanowires can be used to produce a highly selective and sensitive nano-Electronic-nose. In short, single crystalline 1-dimentional oxide nanoprobes can be produced using the electrospinning technique for biological and chemical agent sensing. The nanoprobes can be fabricated with high specificity through manipulation of crystal structure and oxidation state.

EXAMPLES AND EXPERIMENTAL DISCUSSION

Electrospinning

Electrospinning is operated on the principle that the surface tension of a liquid precursor may be broken with the application of a positive potential inducing a jet of polymeric based fibrous structures. Stability and directionality of the jet depend on the electrostatic fields formed between the collector and the needle. The electrospinning setup consists of a high voltage power supply, a programmable syringe pump and a metallic collector plate. The metallic syringe is connected to an anodic clamp from the power supply while the cathodic clamp is connected to the collector. During jet flight the solvent used in the precursor solution evaporates and a dry non-woven mat of fibers can be collected. Several processing conditions can be varied to change the dimensions of these fibers.

Table I below describes and outlines the processing parameters that affect the fiber dimensions. An advantage of this technique is that within this polymer based matrix, dissimilar materials (i.e. metal oxides, biomolecules, etc.) may be encapsulated to form hybrid structures. During electrospinning of metal oxide/polymer hybrid materials the electrospun jet becomes a templating mechanism to which the metal oxide particles assimilate along with the fibers into aligned structures. In this study, two concentrations (0.1M and 0.5M) of molybdenum isopropoxide sol was prepared and mixed with 0.1 mM polyvinylpyrrolidone (1,300,000 Sigma-Aldrich) (ratio 1:4 respectively). The solutions were electrospun in air using a DC voltage power supply (Gamma High Voltage Research, Model ES 30P-6W), a programmable syringe pump (KD Scientific, model 200), and an aluminum collector plate. The electrospinning conditions used are detailed in Table II below.

TABLE I

Electrospinning Processing Conditions

| Precursor Parameters | Polymer Concentration |
| --- | --- |
| | Precursor Viscosity |
| | Ionic Strength |
| | Temperature |
| | Solvent |
| Electrospinning Process Parameters | Needle to collector Distance |
| | Voltage |
| | Flow Rate |

TABLE II

Electrospinning Parameters of $MO_3$ (M:Mo)/polymer hybrids

| $MO_3$ Conc. | Voltage | Distance to Collector | Needle Gauge |
| --- | --- | --- | --- |
| 0.1 M | 15 kV | 55 mm | 22 |
| 0.5 M | 20 kV | 110 mm | 22 |

Calcination of the $MoO_3$/polymer hybrid matrix was carried out from room temperature to 500° C. for two hours then stabilized at 500° C. for four hours (0.1M sample) and for 8 hours (0.5M sample) with a cool down cycle of two hours.

Sensing Experimentation

Electrospun mats of 20/80 0.5M $MoO_3$/PVP and 0.5M $MoO_3$ sol-gel were deposited on alumina substrates with gold interdigitated electrodes with 20 μm spacing. The sensors were placed in a quartz tube and then into a furnace (Lindberg/Blue) and allowed to stabilize in gas mixtures of UHP nitrogen (Praxair) and UHP oxygen (Praxair) at an operating temperature of 450° C. The concentration of oxygen in the inlet stream was maintained at 5% and the furnace was heated at a programmed rate. Exposure tests were carried out for varying concentrations of $NH_3$ (1000 ppm ammonia in nitrogen (BOC gases)). The gases were controlled through 1479

MKS Mass flow controllers with a combined flow rate maintained at 1000 sccm. The change in resistance of the sensor was measured using an Agilent 34401 Å digital multimeter.

Characterization

High Resolution Transmission Electron Microscopy (HR-TEM) was carried out at the Center for Functional Nanomaterials at Brookhaven National Laboratory using a JEOL 4000EX at an accelerating voltage of 400 KV. In parallel studies, conventional Transmission Electron Microscopy studies were carried out using the CM12 STEM (departmental facility) at an accelerating voltage of 120 KV. The nanowires of $MoO_3$ obtained after the heat treatment were dispersed in ethanol and ultrasonically agitated for 5 minutes to achieve uniform dispersion. These were then placed on two types of TEM grids: silicon supported $Si_3N_4$ grids and copper supported holey carbon grids.

Results and Discussion

Figure 2:
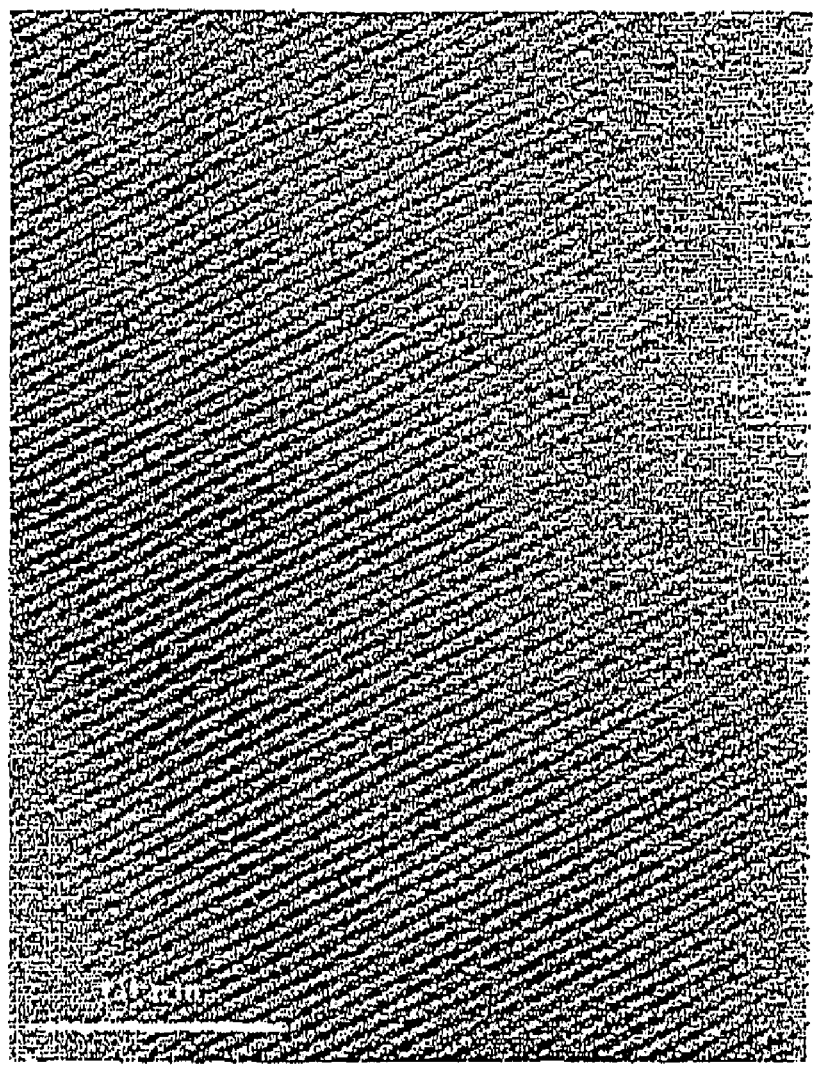
FIG. 2 illustrates the morphology and structure of a $MoO_3$ nanowire on a carbon grid.

Microstructural Characterization:

FIGS. 1 and 2 illustrate the morphology and structure of the nanowires deposited on $Si_3N_4$ and carbon TEM grids respectively; the inset in FIG. 1 is a higher magnification image of the same nanowire revealing its lattice planes. As can be seen from these images, the nanowires are single crystals. Their dimensions are about 10-15 nm in width and 1-2 cm long. The measured d-spacings for the nanowires shown in these figures were 6.944 Å, 3.205 Å and 1.822 Å corresponding to the (020), (021) and the (230) planes of the orthorhombic $MoO_3$ polymorph respectively. The standard JCPDS file corresponding to this structure is 05-0508; the unit cell parameters for the above crystals are a=3.9630 Å, b=13.856 Å, c=3.6966 Å. The crystal belongs to the space-group Pbnm (62).

Figure 3:
FIG. 3 is a TEM micrograph of the as-spun composite nanofibers.

Given that no other study of electrospun metal oxide composites has produced single crystalline nanofibers/nanowires, it is worthwhile to discuss the nature of the underlying mechanism involved in this case. The starting (precursor) material is amorphous $MoO_3$ sol-gel. Differential scanning calorimetry performed on the sol-gel precursor has identified the phase stability fields for the various polymorphs. Heat treating the sol-gel at 500° C. for 8 hrs results in nanostructured polycrystalline grains of the orthorhombic phase polymorph. This is considered to be the "thermodynamically stable" phase of the $MoO_3$ system. The question remains as to why this phase would grow out in a high aspect ratio configuration. The answer may be found in FIG. 3. FIG. 3 is a TEM micrograph of the as-spun composite nanofibers. One may observe the aligned "encapsulation" of the sol-gel component inside the polymeric (PVP) fiber. Therefore, the electrospinning process drives the formation of elongated, amorphous, solgel based fibrous networks of the oxide. It is not clear whether this is the case with all electrospun composites, but it is probably depends on the relative molecular weight of the components, their effective mixing and the viscosity of the solution.

So, one final question remains: why would the resulting oxide nanofibers/wires be single crystals? The answer may lie in the nature of polymorphic reactions in nanocrystalline oxides. Earlier work based on the titania system by Gouma et al. has shown that metastable to stable phase polymorphic reactions in oxides require the formation of critical size nuclei and involve the oriented attachment of nanocrystalline aggregates into large aspect ratio, abnormally large, single crystals of preferred orientation that retain the morphology (contours) of the original aggregate, J. Am. Ceram. Soc., (2001), 84 [3], 619-622; Nanostructured Materials, (1999), 11(8), 1231-1237.

In the case of electrospun composites, the morphology of these aggregates is determined by the presence of the polymeric fiber wall (before its decomposition temperature is reached). Thus, the single crystals of the stable polymorph may grow undisturbed until the sol-gel runs out along the fiber or the fiber path is interrupted. In-situ experiments in the TEM are required to directly capture the process of single crystal nanowire formation. Therefore, it is suggested that there is a particular heat-treatment condition for each metal oxide that should yield single crystal nanowires and which depend on the relative phase stabilities of the various polymorphs of the respective oxide system.

Sensing Tests

The sensing response of the $MoO_3$ nanowire mats to ammonia has been assessed and compared with that of sol-gel based films stabilized under the same conditions. Ammonia has been chosen as the analyte of interest since earlier studies have shown that the orthorhombic phase of $MoO_3$ selectively detects ammonia in the presence of interfering gaseous compounds such as CO, NO, etc. Sensors & Actuators B, (2003), 9, 25-30; Thin Solid Films, (2003), 436, 46-51. The selective gas behavior of this system has implications for the development of "signaling metabolite" detectors for disease diagnosis. Currently, the limiting factor for the development of such biomarker-specific gas sensors is the sensor sensitivity. The use of nanowires (1D configurations) offers the promise of higher signal differential (i.e. sensitivity) for a specific gas concentration, with respect to 3D nanostructures of the same sensing element. The equation for relative sensitivity is: $S=|"R|/Ro*100$ (1) Where "R is the change in resistance on exposure to the gas analyte and Ro is the initial resistance of the sensing element.

Figure 4:
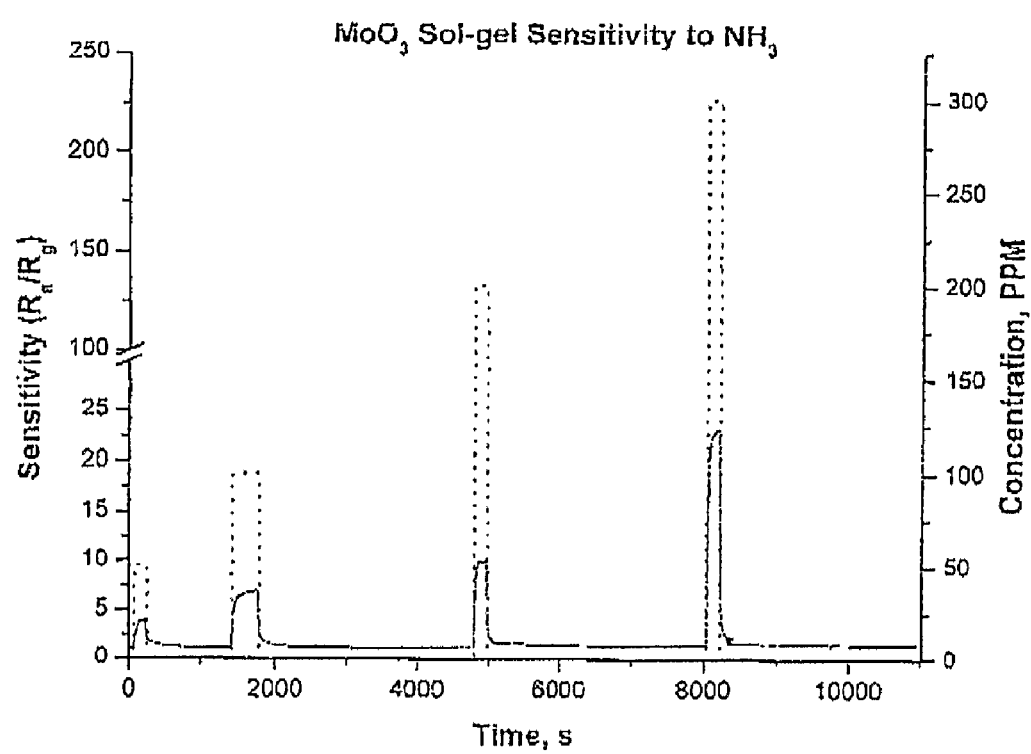
FIG. 4 is a graphic representation of the $MoO_3$ nanowires to 50 ppm, 100 ppm, 200 ppm and 300 ppm $NH_3$.
Figure 5:
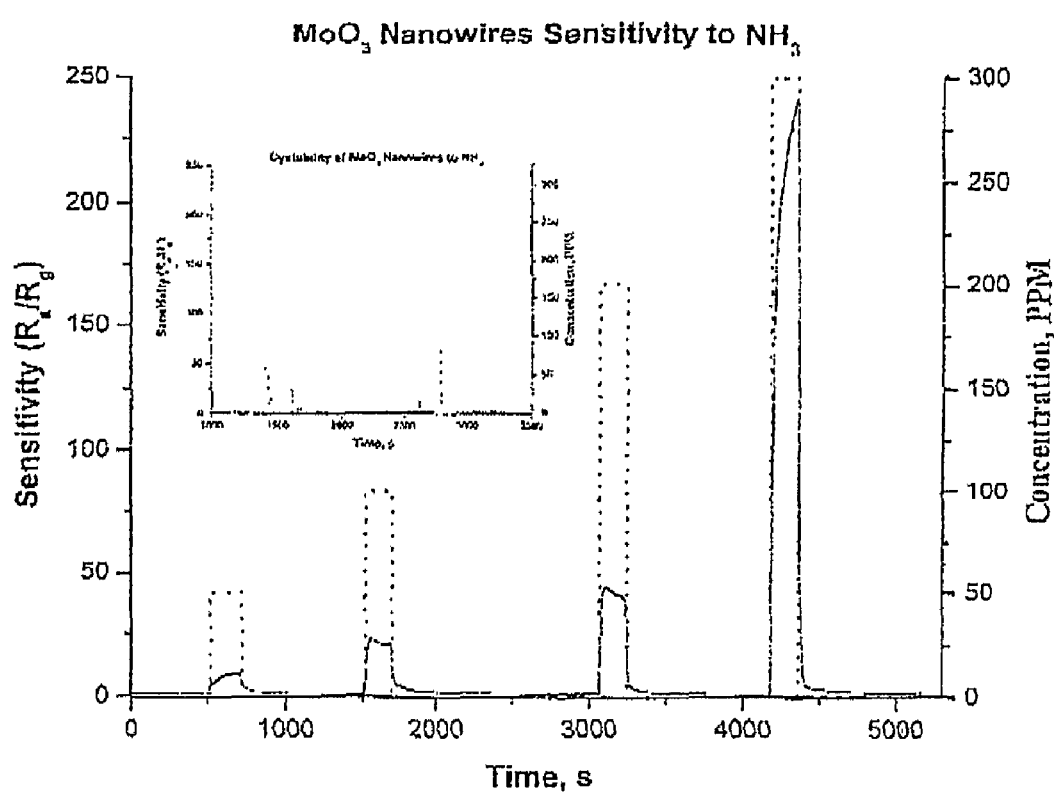
FIG. 5 is a graphic representation of the sensitivity of anaocrystalline $MoO_3$ sol-gel films to 50 ppm, 100 ppm, 200 ppm and 300 ppm $NH_3$.

FIGS. 4 and 5 show the sensing response of the nanowires and sol-gel films to varying concentrations of $NH_3$. The sensitivities as opposed to the original resistance plots are provided here for comparison purposes. Both the nanowire sensor and the sol-gel thin film were heat stabilized at 500° C. for 8 hrs in air prior to the sensing measurements to obtain an orthorhombic crystal structure.

The sensing experiments were carried out at operating temperatures of 450° C. in order to avoid any undesirable polymorphic transformations in the metal oxide. The $NH_3$ concentration was varied from 50 ppm to 300 ppm in a background mixture of 80% $N_2$ and 10% $O_2$. The gas pulses were 3 minutes long and were repeated to ensure reproducibility in the sensing response. Upon the introduction of a reducing gas like ammonia the resistance decreased in both the nanowires and the sol-gel film, confirming thereby that both the sensors were n-type semiconducting oxides.

Table III shows the sensitivity values of both the sensors for different concentrations of $NH_3$. The response times for the nanowires are of the order of a few seconds while the recovery times (time taken to return to 90% of the baseline without any bias) are of the order of minute, for all concentrations of $NH_3$. The sol-gel films on the other hand have response (2-4 minutes) and recovery times (20-30 minutes) that are considerably larger than the nanowires, and the recovery slows down as the concentration of the gas increases from 50 ppm to 300 ppm.

TABLE III

Sensitivity of 0.5 $MoO_3$ sensor matrices to $NH_3$

| Sensor | 50 ppm | 100 ppm | 200 ppm | 300 ppm |
| --- | --- | --- | --- | --- |
| $MoO_3$ sol-gel | 0.75 | 0.85 | 0.89 | 0.94 |
| $MoO_3$ nanowires | 0.88 | 0.95 | 0.97 | 0.99 |

Summarizing, the sensoric nature of the nanowires renders these configurations inherently stable, more sensitive and respond faster to ammonia compared to the nano-structured polycrystalline sol-gel thin film sensors of the same composition and phase. This is due to the fact that the quasi one-dimensional nano-structures have well-defined crystallographic orientations and larger surface-area to volume ratios. The specific interactions of the nanowires with the gas need to be evaluated further.

Accordingly, the technique of the invention produces single crystal $MoO_3$ nanowires using the electrospinning technique. The single crystal $MoO_3$ nanowires produced have many different applications, one application in particular for these nanostructures is gas sensing. As stated above, using nanocrystalline metal oxide based sensor technologies for gas sensing, has only limited affects due to their limited gas selectivity and a large amount of cross-interference from other gases. In contrast, single crystal $MoO_3$ nanowires yields improved sensitivity, stability, and response times over conventional nanocrystalline metal oxide based sensor technologies. It is expected that these single-crystal nanowires will be the building blocks of medical diagnostic devices.

While this invention has been particularly shown and described with reference to preferred embodiments thereof, it will be understood by those skilled in the art that various changes in form and details may be made therein without departing from the scope of the invention encompassed by the appended claims.

What is claimed is:

1. A method for producing electrospun single crystal $MoO_3$ nanowires,
   the method comprising steps of:
   (i) centrifuging a $MoO_3$ solution in a solvated mixture;
   (ii) mixing the centrifuged $MoO_3$ mixture with a PVP solution to produce a solution for electrospinning;
   (iii) electrospinning the solution of step (ii) to produce films;
   (iv) calcinating the films of step (iii) to produce a calcined mat wherein said calcinating is performed at 25° C. to 500° C. for about two hours, followed by stabilization for approximately 8 hours at 500° C. and then a cooling down period from 500° C. to 25° C. for about 2 hours in order to obtain a calcined mat;
   (v) dissolving the calcined mat in a solvent to produce a dissolved polymer solution; and
   (vi) depositing the dissolved polymer solution onto an alumina substrate forming a thin film of single crystal nanowires.

2. The method of claim 1 wherein in step (i), $MoO_3$ is dissolved in butanol at a 0.5 molar concentration.

3. The method of claim 1 wherein the solution of step (ii) is electrospun onto aluminum foil in air at a voltage of about 20 kv with a needle distance of about 100 mm, and a needle gauge of about 22 to produce films.

4. The method of claim 1 wherein said calcined mat is dissolved in ethanol to produce a dissolved polymer solution.

* * * * *